US008513010B2

(12) United States Patent
Nieda et al.

(10) Patent No.: US 8,513,010 B2
(45) Date of Patent: Aug. 20, 2013

(54) DENDRITIC CELLS PULSED WITH A BISPHOSPHONATE

(75) Inventors: Mie Nieda, Tokyo (JP); Manami Isogai, Saitama (JP); Kazuhiro Kakimi, Tokyo (JP)

(73) Assignee: Medinet Co. Ltd. (JP)

( * ) Notice: Subject to any disclaimer, the term of this patent is extended or adjusted under 35 U.S.C. 154(b) by 1081 days.

(21) Appl. No.: 11/631,660

(22) PCT Filed: Jul. 7, 2005

(86) PCT No.: PCT/JP2005/012971
§ 371 (c)(1),
(2), (4) Date: May 3, 2007

(87) PCT Pub. No.: WO2006/006638
PCT Pub. Date: Jan. 19, 2006

(65) Prior Publication Data
US 2007/0190169 A1    Aug. 16, 2007

(30) Foreign Application Priority Data

Jul. 8, 2004 (JP) .................................. 2004-229991

(51) Int. Cl.
*C12N 5/0784* (2010.01)
(52) U.S. Cl.
USPC .......................... 435/372; 435/325; 435/372.3
(58) Field of Classification Search
USPC ....................................... 435/372, 372.3, 325
See application file for complete search history.

(56) References Cited

U.S. PATENT DOCUMENTS

| 6,821,778 | B1 | 11/2004 | Engleman et al. | |
|---|---|---|---|---|
| 2003/0118637 | A1* | 6/2003 | Jordan et al. | 424/450 |
| 2005/0048646 | A1 | 3/2005 | Nieda et al. | |
| 2009/0104161 | A1 | 4/2009 | Nieda et al. | |
| 2012/0107292 | A1 | 5/2012 | Nieda et al. | |
| 2012/0308986 | A1 | 12/2012 | Deng et al. | |

FOREIGN PATENT DOCUMENTS

| JP | 2002-525606 A | 8/2002 |
|---|---|---|
| JP | 2003-511064 A | 3/2003 |

OTHER PUBLICATIONS

Pfeiffer et al. Dendritic cells generated from the blood of patients with multiple myeloma are phenotypically and functionally identical to those similarly produced from healthy donors. British Journal of Haematology, 1997, 98:973-982.*
Raje et al. Introduction: the evolving role of bisphosphonate therapy in multiple myeloma. Blood, Jul. 15, 2000, vol. 96, No. 2. p. 381-383.*
Ju et al., "Review of Human DC Subtypes," *Dendritic Cell Protocols*, Methods in Molecular Biology 595, Chapter 1, pp. 3-20, 2010.
Pickl et al., "Molecular and Functional Characteristics of Dendritic Cells Generated from Highly Purified CD14+ Peripheral Blood Monocytes," *Journal of Immunology*, 1996, pp. 3850-3859, vol. 157, No. 9.
Wu et al., "Development of Dendritic Cell System," *Cellular & Molecular Immunology*, 2004, pp. 112-118, vol. 1, No. 2.
Kato et al., "Requirement of Species-Specific Interactions for the Activation of Human γδ T Cells by Pamidronate", *The Journal of Immunology*, vol. 170, 2003 (pp. 3608-3613).
Sanders et al., "Quantitative Structure-Activity Relationships for γδ T Cell Activation by Bisphosphonates", *J. Med. Chem.*, vol. 47, 2004 (pp. 375-384).
Von Lilienfeld-Toal et al., "Coculture with dendritic cells promotes proliferation but not cytotoxic activity of γ/δ T cells", *Immunology Letters*, vol. 99, 2005 (pp. 103-108).
Yoshida et al., "Evaluation of the skin sensitization potential of chemicals using expression of co-stimulatory molecules, CD54 and CD86, on the naïve THP-1 cell line", *Toxicology in Vitro*, vol. 17, 2003 (pp. 221-228).
Supplementary European Search Report based on Application No. EP 05 76 0126, date of completion of the search Jan. 16, 2009 (2 pgs.).
Kunzmann et al., "Crucial Role of Monocytes in Aminobisphosphonate Recognition by γδ T Cells", *Blood, Journal of the American Society of Hematology*, vol. 102, No. 11, Nov. 16, 2003 (p. 39b).
Miyagawa et al., "Essential Requirement of Antigen Presentation by Monocyte Lineage Cells for the Activation of Primary Human γδ T Cells by Aminobisphosphonate Antigen", *The Journal of Immunology*, vol. 166, No. 9, May 1, 2001 (pp. 5508-5514).
PCT International Search Report based on International Application No. PCT/JP2005/012971, date of mailing of the International Search Report Oct. 18, 2005 (2 pgs.).
Tajima et al., "Immunomodulatory effects of cyclosporin A on human peripheral blood dendritic cell subsets", *Immunology*, vol. 108, No. 3, Mar. 2003 (pp. 321-328).
Valladeau et al., "Immature Human Dendritic Cells Express Asialoglycoprotein Receptor Isoforms for Efficient Receptor-Mediated Endocytosis", *The Journal of Immunology*, vol. 167, No. 10, Nov. 15, 2001 (pp. 5767-5774).
Yoneda, "Bisphosphonate no Sayo Mechanism to Potential", *Igaku no Ayumi*, vol. 189, No. 2, Apr. 10, 1999 (pp. 95-100).
Carratelli, et al., "Porins and lipopolysaccharide from *Salmonella typhimurium* regulate the expression of CD80 and CD86 molecules on B cells and macrophages but not CD28 and CD152 on Tcells," *Clinical Microbiology and Infection*, vol. 9, No. 11, Nov. 2003 (pp. 1104-1111), European Society of Clinical Microbiology and Infections Diseases, Napoli, Italy.
McLlroy, et al., "Investigation of human spleen dendritic cell phenotype and distribution reveals evidence of in vivo activation in a subset of organ donors", *Blood Journal* Jun. 1, 2001, (pp. 3470-3477) vol. 97, No. 11, American Society of Hematology, Washington, D.C.

(Continued)

*Primary Examiner* — Taeyoon Kim
(74) *Attorney, Agent, or Firm* — Foley & Lardner LLP

(57) ABSTRACT

The present invention provides dendritic cells capable of efficiently activating and/or proliferating γδ T-cells in vivo and/or in vitro, pharmaceutical compositions comprising said dendritic cells, therapeutic methods and γδ T-cell culture methods utilizing said dendritic cells. By pulsing immature dendritic cells derived from peripheral blood monocytes with a bisphosphonate-based bone metabolism improving drug to enable the cells to activate γδ T-cells, and cultivating them with a cell subset containing γδ T-cells, γδ T-cells can be activated and/or proliferated. This allows for easy proliferation of γδ T-cells without burdening a patient, leading to practical applications of immune cell therapies that utilize γδ T-cells.

18 Claims, 2 Drawing Sheets

(56) References Cited

OTHER PUBLICATIONS

O'Doherty et al., "Human blood contains two subsets of dendritic cells, one immunologically mature and the other immature", *Immunology* 1994 82: (pp. 487-493), Laboratory of Cellular Physiology and Immunology, The Rockefeller University, New York, New York.

Shen, et al., "Ganglioside GD1a impedes lipopolysaccharaide-induced maturation of human dendritic cells", *Cellular Immunology* 220 2002 (pp. 125-133), Elsevier Science, Center for Cancer Research, Washington, D.C.

Wang, et al., "Gold sodium thiomalate suppresses the differentiation and function of human dendritic cells from peripheral blood monocytes", Clinical and Experimental Rheumatology 2002; (pp. 683-688) vol. 20, Department of Clinical Pathology and Immunology, Kobe University Graduate School of Medicine, Kobe, Hyogo, Japan.

Office Action for JP 2006-529100, dated Jan. 21, 2011 (4 pgs.).

Japanese Office Action for JP 2006-529100, dated Jun. 21, 2011, 4 pages.

Yang et al., "Rab7b, a novel lysosome-associated small GTPase, is involved in monocytic differentiation of human acute promyelocytic leukemia cells", Biochemical and Biophysical Research Communications 318 (2004),May 18, 2004, p. 792-799.

Ancuta et al., "CD14+ CD16++ cells derived in vitro from peripheral blood monocytes exhibit phenotypic and functional dendritic cell-like characteristics", Eur J. Immunol., vol. 30, p. 1872-1883 (2000).

Baey et al., "Phenotype and function of human dendritic cells derived from M-DC8+ monocytes", Eur. J. Immunol vol. 31, p. 1646-1655 (2001).

Inaba et al., Clinical Immunology, vol. 30, No. 3, p. 423-429 (1998).

Molecular Medicine, vol. 38 p. 180-188 (2001).

Japanese Office Action for JP 2012-151970, Aug. 28, 2012, 2 pages.

Santiago-Schwarz, "Positive and Negative Regulation of the Myeloid Dendritic Cell Lineage," Journal of Leukocyte Biology, vol. 66, Aug. 1999, pp. 209-216.

Abstract for Isogai et al., 01CStudy of proliferative capacity and function of 3B33B4T cells by dendritic cells pulsed with pamidronate,01D The 26th Annual Meeting of the Japanese Research Society for Surgical Cancer Immunology, May 19-20 (2005).

Abstract for Isogai et al., 01CStudy of proliferative capacity of 3B33B4T cells by dendritic cells pulsed with pamidronate,01D The 42th Annual Meeting of the Japan Society of Clinical Oncology, Sep. 29 (2004).

Abstract for Takahara et al., 01CStudy of proliferative capacity and function of 3B33B4T cells by dendritic cells pulsed with pamidronate,01D The 3rd Meeting of Japan Research Association for Immunotherapeutics, Dec. 4 (2004).

\* cited by examiner

FIG. 1

| Dendritic Cells | Bisphosphonate | Final Concentration ($\mu$M) | Proportion of $\gamma\delta$ T-cells (%) | Total Number of Cells ($\times 10^6$) | Number of $\gamma\delta$ T-cells ($\times 10^6$) |
|---|---|---|---|---|---|
| Immature Dendritic Cells | Control | 0 | 4.2 | 5.5 | 0.23 |
| | Aredia | 10 | 69.7 | 11 | 7.67 |
| | Onclast | 10 | 79.8 | 8.2 | 6.54 |
| | Zometa | 1 | 75.9 | 11.6 | 8.80 |
| Mature Dendritic Cells | Control | 0 | 10.4 | 9.6 | 1.00 |
| | Aredia | 10 | 38.8 | 11.1 | 4.31 |
| | Onclast | 10 | 34.3 | 10.4 | 3.57 |
| | Zometa | 1 | 63.6 | 10.3 | 6.55 |

DENDRITIC CELLS PULSED WITH A BISPHOSPHONATE

BACKGROUND OF THE INVENTION

1. Technical Field

The present invention relates to dendritic cells pulsed with bisphosphonate-based bone metabolism improving drugs (hereinafter referred to as bisphosphonates). The present invention also relates to pharmaceutical compositions comprising said dendritic cells, therapeutic methods and γδ T-cell culture methods utilizing said dendritic cells.

2. Technical Background

Dendritic cells work as antigen-presenting cells to present antigens, through phagocytosis and fragmentation, as antigenic epitopes on Major Histocompatibility Complex (MHC) molecules at their cell surface. When dendritic cells come in contact with T-cells in a lymph node, the T-cells recognize these antigenic epitopes.

In T-cells, αβ T-cells expressing αβ T-cell receptors and γδ T-cells expressing γδ T-cell receptors are present. The αβ T-cells primarily assume the responsibility for acquired immunity, while the γδ T-cells work as effector cells for immune responses to particular bacterial infections such as tuberculosis, as well as tumors, and mainly assume the responsibility for natural immunity.

It has recently been found that γδ T-cells also have cytotoxic activity against cancer cells, drawing attention to the development of immunotherapy utilizing the powerful anti-tumor activity possessed by γδ T-cells. The vast majority of T-cells generally present in blood, however, are αβ T-cells; γδ T-cells account for a mere 1-5%. Accordingly, as a method to proliferate γδ T-cells, the γδ T-cells that are separated using magnets and the like are cultured in vitro and returned to the body.

It is known that γδ T-cells are also activated and/or proliferated by nonpeptide antigens; they are known to be activated and/or proliferated by alkaloids such as alkylamines, as well as pyrophosphate monoesters and bisphosphonates.

Above all, methods to cultivate γδ T-cells in vitro utilizing bisphosphonates have been considered in various studies, but failed to produce sufficient numbers of γδ T-cells. An attempt to obtain a sufficient number of γδ T-cells suitable for a treatment meant an increase in the amount of blood collected from a patient, which also increased the burden placed on the patient. Accordingly, there exists a need to establish a technique to easily obtain a sufficient number of γδ T-cells not only in vitro, but also in vivo.

SUMMARY OF THE INVENTION

The present invention was created in view of the aforementioned circumstances to provide dendritic cells capable of efficiently activating and/or proliferating γδ T-cells in vivo and/or in vitro, pharmaceutical compositions comprising said dendritic cells, therapeutic methods of the pharmaceutical compositions and γδ T-cell culture methods utilizing said dendritic cells.

As a result of research in solving the aforementioned problems, the inventors found that γδ T-cells can be activated and/or proliferated by using dendritic cells, which are normally used for CTL induction, pulsed with bisphosphonates, instead of directly stimulating γδ T-cells with bisphosphonates. Furthermore, the inventors found that, unlike the case of inducing antigen-specific αβ T-cells using a disease antigen peptide, γδ T-cells, unexpectedly, can be suitably activated and/or proliferated by utilizing immature dendritic cells, thereby completing the present invention.

The present invention enables easy proliferation of γδ T-cells without imposing a burden on a patient, leading to practical applications of immune cell therapies that utilize γδ T-cells.

The present invention is described below.

(1) Dendritic cells having been pulsed with a bisphosphonate;
(2) The dendritic cells of said (1), wherein said dendritic cells are immature dendritic cells;
(3) The dendritic cells of said (1) or (2), wherein said bisphosphonate is any one of pamidronic acid, alendronic acid, zoledronic acid, risedronic acid, ibandronic acid, incadronic acid, etidronic acid, their salts and/or their hydrates;
(4) A pharmaceutical composition comprising dendritic cells pulsed with a bisphosphonate;
(5) The pharmaceutical composition of said (4), wherein said dendritic cells are immature dendritic cells;
(6) The pharmaceutical composition of said (4) or (5), wherein said bisphosphonate is any one of pamidronic acid, alendronic acid, zoledronic acid, risedronic acid, ibandronic acid, incadronic acid, etidronic acid, their salts and/or their hydrates;
(7) A therapeutic method wherein dendritic cells pulsed with a bisphosphonate are administered;
(8) The therapeutic method of said (7), wherein said dendritic cells are immature dendritic cells;
(9) The therapeutic method of said (7) or (8), wherein said bisphosphonate is any one of pamidronic acid, alendronic acid, zoledronic acid, risedronic acid, ibandronic acid, incadronic acid, etidronic acid, their salts and/or their hydrates;
(10) The therapeutic method of any of said (7)-(9), wherein the therapy is for treating cancers and/or infectious diseases;
(11) The therapeutic method of any of said (7)-(11) [sic], wherein said dendritic cells are autologous;
(12) A γδ T-cell culture method wherein dendritic cells pulsed with a bisphosphonate are added;
(13) The γδ T-cell culture method of said (12), wherein said dendritic cells are immature dendritic cells; and
(14) The γδ T-cell culture method of said (12) or (13), wherein said bisphosphonate is any one of pamidronic acid, alendronic acid, zoledronic acid, risedronic acid, ibandronic acid, incadronic acid, etidronic acid, their salts and/or their hydrates.

BRIEF DESCRIPTION OF THE DRAWINGS

FIG. 1 shows the results of Example 3. Controls (dendritic cells not pulsed with a bisphosphonate), dendritic cells pulsed with Aredia, Onclast, and Zometa were respectively cocultivated with the reacted cells. The number of cells measured seven days later using a hemocytometer; the proportion of γδ T-cells measured using a flow cytometer; and the number of γδ T-cells calculated from the two figures are shown.

Figure 2:
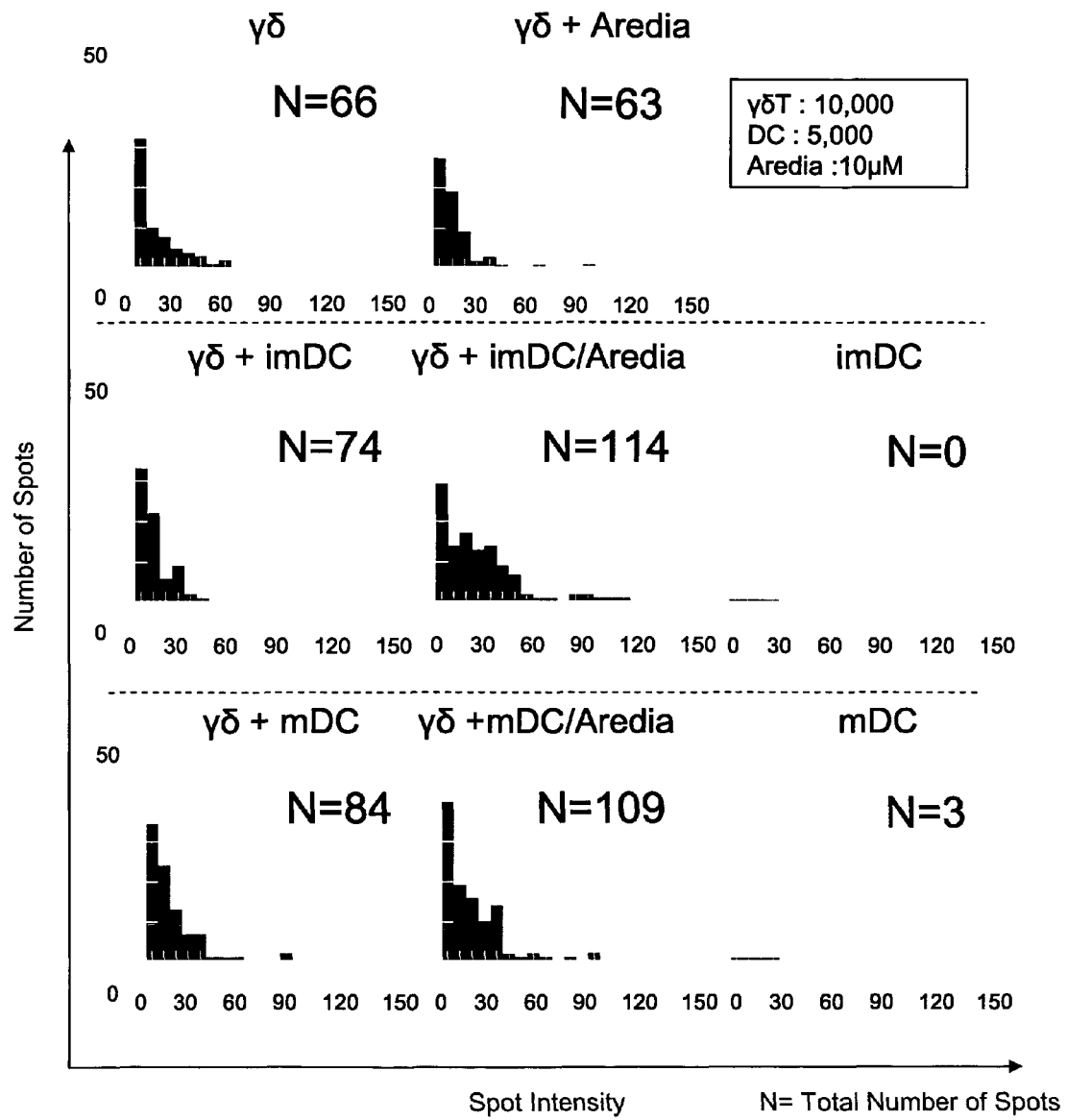
FIG. 2 shows the results of Example 5. The ordinate indicates the number of spots and the abscissa indicates the intensity of the spots. As negative controls, the IFN-γ produced by γδ T-cells alone; γδ T-cells and Aredia; and the dendritic cells alone are shown.

BEST MODE OF THE INVENTION (1) First Embodiment: Preparation of the Dendritic Cells of the Invention The dendritic cells of the invention will be explained in detail first.

The dendritic cells of the present invention refer to dendritic cells having been pulsed with a bisphosphonate.

As the dendritic cells of the invention, immature dendritic cells, mature dendritic cells, or the mixture of the two may be used. It is preferable, however, to use immature dendritic cells, since they are capable of more suitably activating and/or proliferating γδ T-cells.

Moreover, any bisphosphonate may be used as long as it functions as a bone-resorption inhibitor and is generally used as a drug to treat osteoporosis. Examples include pamidronic acid, a salt thereof and/or their hydrates (for example, pamidronate disodium pentahydrate (Aredia by Novartis Pharma)), alendronic acid, a salt thereof and/or their hydrates (for example, alendronate sodium trihydrate (Onclast by Banyu Pharmaceutical)), zoledronic acid, a salt thereof and/or their hydrates (for example, zoledronate sodium hydrate (Zometa by Novartis Pharma)), risedronic acid, a salt thereof and/or their hydrates (for example, risedronate sodium hydrate), ibandronic acid, a salt thereof and/or their hydrates (for example, ibandronate sodium), incadronic acid, a salt thereof and/or their hydrates (for example, incadronate disodium), etidronic acid, a salt thereof and/or their hydrates (for example, etidronate disodium). Above all, pamidronic acid, alendronic acid, zoledronic acid, their salts and/or their hydrates are particularly preferable.

Next, the method of preparing the dendritic cells of the present invention will be explained in detail.

A sample is obtained first in order to obtain precursors of dendritic cells. Peripheral blood, bone marrow, umbilical cord blood or the like can be used as a sample. Considering the ease of collection and the minimal burden imposed on the patient, utilizing peripheral blood is preferable.

It is preferable to collect an amount of blood that does not burden the donor. As a method of collection, whole blood can be collected utilizing a vacuum blood tube or the like. Heparin or citric acid may be added so that the collected blood does not coagulate. In the case wherein a large number of cells is required, peripheral blood monocytes can be directly obtained by a method to collect the mononuclear component using a component collection system.

Mononuclear cells, or the precursors of dendritic cells, are then separated from the blood collected. Any method for separating nucleated cells from red blood cells may be used. For example, the Ficoll separation method, i.e., a Ficoll-Paque density gradient, or elution is commonly used.

In order to remove platelets and the like, it is preferable to clean the collected cells several times using a culture medium, physiological saline, phosphate buffered saline (hereinafter referred to as PBS) or the like.

Next, the dendritic cell precursors are separated from the mononuclear cells collected.

Since CD14 is a known marker expressed in the dendritic cell precursors, a method to isolate and collect monocytes (CD14-positive cells) utilizing the Magnetic Cell Sorting (Miltenyi Biotec; hereinafter referred to as MACS) is preferred since it is simple, and yields a high cell collection rate.

Another method may also be used, wherein the mononuclear cells collected are cultivated for at least one hour in a culture flask under the conditions of 34-38° C., more preferably 37° C., and 2-10% CO2, more preferably 5% CO2, and the cells deposited are used as the dendritic cell precursors.

This is followed by differentiating the dendritic cell precursors into immature or mature dendritic cells. AIM-V medium (Invitrogen) is used as a culture medium.

In addition to AIM-V medium, any commercially available medium used in cell cultivation, such as RPMI-1640 Medium (Invitrogen), Dulbecco's Modified Eagle Medium (Invitrogen; hereinafter referred to as DMEM), TIL (Immuno-Biological Laboratories Co., Ltd.), epidermal keratinocyte medium (Kojin Bio, Ltd.; hereinafter referred to as KBM), and Iscove's Medium (Invitrogen; hereinafter referred to as IMEM), may be used. Moreover, 5-20% bovine serum, fetal bovine serum (hereinafter referred to as FBS), human plasma or the like may be added as needed.

In the case of immature dendritic cells, they are obtained by adding a differentiation-inducing factor to the culture medium and cultivating the dendritic cell precursors.

Any cytokine may be used as a differentiation-inducing factor; for example, granulocyte-macrophage colony-stimulating factor (hereinafter referred to as GM-CSF), interleukin-4 (hereinafter referred to as IL-4), stem cell factor (hereinafter referred to as SCF), IL-13, tumor necrosis factor α (hereinafter referred to as TNF-α) and the like can efficiently induce the differentiation of immature dendritic cells. It is also preferable to add IL-1, IL-2, IL-3 and the like as needed. More preferably, the use of a combination of GM-CSF and IL-4 enables efficient induction.

The cultivation is carried out under the conditions of 34-38° C., more preferably 37° C., and 2-10% $CO_2$, more preferably 5% $CO_2$; the cultivation duration is preferably 5-7 days.

In the case of obtaining mature dendritic cells, an additional differentiation-inducing factor is added on the 5th-7th day after starting the culture for further cultivation.

Any cytokine may be used as a differentiation-inducing factor; it is preferable to use, for example, GM-CSF, IL-4, SCF, IL-1β, IL-6, IL-13, INF-α, prostaglandin $E_2$ (hereinafter referred to as $PGE_2$) and the like to efficiently induce the differentiation of mature dendritic cells. IL-1, IL-2, IL-3 and the like are preferably added as needed. More preferably, employing a combination of GM-CSF, IL-4, IL-6, IL-1β, $PGE_2$ and TNF-α enables efficient induction.

The cultivation is carried out under the conditions of 34-38° C., more preferably 37° C., and 2-10% $CO_2$, more preferably 5% $CO_2$; the duration is preferably 24-48 hours.

Moreover, a method for obtaining immature or mature dendritic cells by collecting hematopoietic stem cells (CD34-positive cells) as dendritic cell precursors and adding GM-CSF and TNF-α, as well as flt-3 Ligand (FL), c-kit Ligand (SCF) or trombopoetin (TPO), singly or in combination, or a method of directly collecting dendritic cell fractions from blood or separated peripheral blood monocytes by using a density-gradient medium such as Percoll, may also be used.

To the immature or mature dendritic cells obtained, a bisphosphonate is added and cultured to prepare stimulating cells (dendritic cells pulsed with a bisphosphonate). The concentration of the bisphosphonate added is preferably 0.1-30μM, more preferably 1-10 μM.

The duration of pulsing the cells with the bisphosphonate is preferably 1-36 hours, more preferably 12 hours.

Since the dendritic cells obtained in this manner have the ability to activate and/or proliferate γδ T-cells, they can be used as a pharmaceutical composition capable of activating and/or proliferating γδ T-cells either in vitro or in vivo. When used in vitro, they can be used as a composition capable of activating and/or proliferating γδ T-cells. When used in vivo, they can be used as a dendritic cell vaccine capable of activating and/or proliferating γδ T-cells after rinsing and removing free bisphosphonate. In either case, in vitro or in vivo, a cytokine (for example, IL-2), a protein (for example, albumin) or the like may be added as needed.

(2) Second Embodiment: Pharmaceutical Composition Comprising the Dendritic Cells of the Invention The therapeutic method utilizing the dendritic cells of the invention will be explained below.

The dendritic cells obtained in the first embodiment are collected by centrifugation or the like.

The collected cells are washed. Any washing solution may be used as long as it is isosmotic and suitable for use as a pharmaceutical composition. Considering the subsequent administration to a patient, the use of physiological saline, PBS or the like is preferable.

When suspended in physiological saline, the dendritic cells collected become usable as a pharmaceutical preparation for administration. In addition, a cytokine may be added as needed.

The number of cells administered can be properly selected in accordance with the condition of the patient; normally, however, the number of cells is preferably $10^6$-$10^{12}$/person, more preferably at least $10^7$/person.

The preparation can be administered by intravenous, intradermal or hypodermic injection, injected into an affiliated lymph node, directly injected into a lesion, or drip-fed for general administration. It is also possible to inject the preparation into an artery in the vicinity of a lesion.

By administering the dendritic cells of the present invention in this manner, the γδ T-cells in the patient's body can be activated. Since γδ T-cells have nonspecific cytotoxic activity, they can be used in various treatments, for example, treating cancers and infectious diseases. One benefit of using dendritic cells in the form of a vaccine is a circumvention of the problem caused by directly administering a bisphosphonate. A bisphosphonate's reaction to γδ T-cells in the body is weakened and dissipated as the number of administrations increases, making the bisphosphonate incapable of repeatedly proliferating γδ T-cells. By pulsing dendritic cells with a bisphosphonate for use as a vaccine prevents this from occurring.

(3) Third Embodiment: The γδ T-Cell Culture Method Using the Invention's Dendritic Cells The γδ T-cell culture method of the invention will be explained in detail below.

The dendritic cells obtained in the first embodiment and the responding cells are disseminated in a culture container.

The responding cells here refers to a cell subset containing γδ T-cells; mononuclear cells derived from peripheral blood and the like are preferable.

There is no particular limitation for the container used; a plate, laboratory dish, flask, bag or the like normally employed in cultivation in the art may be used. The concentration of the individual cell subsets disseminated may be freely set in accordance with the situation.

AIM-V medium is used to culture the dendritic cells and the responding cells. In addition to AIM-V medium, any commercially available culture medium used in cell cultivation, such as RPMI-1640 medium, DMEM, TIL, KBM, and IMEM, may be used. Moreover, 5-20% bovine serum, FBS, human plasma, cytokine or the like may be added as needed.

The cultivation is carried out under the conditions of 34-38° C., more preferably 37° C., and 2-10% $CO_2$, more preferably 5% $CO_2$; the cultivation duration is preferably 5-8 days, more preferably 7 days.

The numbers of dendritic and responding cells disseminated can be set depending on the container used and the purpose of the application. The mixing proportions of the dendritic and responding cells can be properly set in accordance with the situation; considering the purpose, which is to increase the proportion of γδ T-cells in the reacted cells, the number of dendritic cells is preferably set smaller than the responding cells.

The present invention enables the collection of a cell population containing activated γδ T-cells of high purity, in mass quantity and in a simple manner, without having to follow the complicated selection and purification processes which were required by prior art techniques to obtain γδ T-cells. Moreover, the cell population obtained in this manner can be used as it is in immune cell therapies. When the activated γδ T-cells are used in such immune cell therapies, high levels of therapeutic effect against tumors and infectious diseases are expected.

One benefit of activating and/or proliferating γδ T-cells in vitro is a circumvention of the problem associated with directly administering a bisphosphonate, whose reaction to γδ T-cells in the body weakens and dissipates when the number of administrations increases so that it is incapable of repeatedly proliferating γδ T-cells. Activating and/or proliferating γδ T-cells in vitro for administration can prevent this from occurring.

(4) Fourth Embodiment: Pharmaceutical Composition Comprising the γδ T-Cells Obtained by the Invention The method of administering the γδ T-cells obtained above to a patient will be explained next.

The γδ T-cells obtained by the method described in the third embodiment are collected by centrifugation and the like.

The cells collected are washed. Any washing solution may be used as long as it is isosmotic and suitable for use as a pharmaceutical preparation; considering the subsequent administration to a patient, the use of physiological saline, PBS or the like is preferable.

When suspended in physiological saline, the γδ T-cells collected become usable as a preparation for administration. In addition, a cytokine may be added as needed.

The number of cells administered can be properly selected in accordance with the condition of the patient; normally, however, the number of cells is preferably $10^8$-$10^{12}$/person, more preferably at least $10^9$/person.

It can be administered by intravenous, intradermal or hypodermic injection, injected into an affiliated lymph node, directly injected into a lesion, or drip-fed for general administration. The preparation can also be injected into an artery in the vicinity of a lesion.

EXAMPLES

The present invention will be explained in detail with reference to examples; the present invention, however, is obviously not limited to these examples.

Example 1

<Collection and Preparation of Dendritic Cells>

From the 30 ml of peripheral blood collected from a healthy donor mononuclear cells were collected using a density gradient medium for separating blood cells. The cells collected were washed several times to remove platelets and the like, and CD14-positive cells were isolated using MACS.

The dendritic cell precursors obtained were differentiated into dendritic cells. AIM-V medium with 10% FBS added thereto was used as a culture medium. To the medium 500 U/mL of GM-CSF (IMMUNEX) and 500 mL of IL-4 (Osteogenetics GmbH) were added. Immature dendritic cells were obtained in 5-7 days after starting the culture. Moreover, on the $5^{th}$-$7^{th}$ day after starting the culture, 100 U/mL of IL-6 (R & D Systems), 10 ng/mL of IL-1β (CHEMICON), 10 ng/mL of TNF-α (PHARMINGEN), and 1 µg/ml of $PGE_2$ (SIGMA) were added for further cultivation. Mature dendritic cells were collected 24-48 hours later.

Example 2

<Confirmation of the Condition of the Dendritic Cells>

The antigens on the surface of the dendritic cells prepared were detected using a flow cytometer (Epics XL-MCL, Beckman Coulter). To the cells to be measured, suspended in PBS, target antibodies were added and stained for 15 minutes at 4° C. in a shaded condition. The antibodies used are PE-labeled anti-CD14, anti-CD83 and anti-HLA-DR antibodies (Beckman Coulter). As negative controls, the isotypes of the respective antibodies were used. The stained cells were washed with PBS and measured by using the Epics XL-MCL.

The results showed that the cells cultured with GM-CSF and IL-4 were CD14 and CD83 negative, HLA-DR positive, and confirmed to be an immature dendritic cell population. The cells cultivated with GM-CSF, IL-4, IL-6, IL-1β, TNFα, and $PGE_2$ were positive except for CD14, and confirmed to be a mature dendritic cell population.

Example 3

<Proliferation of γδ T-Cell with Dendritic Cells>

To the suspensions containing the immature or mature dendritic cells derived from peripheral blood prepared in Example 1, bisphosphonates, Aredia, Onclast and Zometa, were added to achieve the concentrations of 10 μM, 10 μM and 1 μM, respectively, and cultured for about 12 hours to prepare stimulating cells (dendritic cells pulsed with bisphosphonates). As a negative control, dendritic cells cultured without adding a bisphosphonate were used.

These stimulating cells, $5 \times 10^5$ each, were respectively cultivated in mixed cultures of $2 \times 10^6$ reacted cells using a 24-well plate (SUMILON) to a total volume of 1 mL (the ratio of reacted cells to stimulating cells was 4 to 1). The cells remaining after isolating the CD14-positive cells in Example 1 (CD14-negative cell population, mainly T-cell population), which had been suspended in AIM-V medium containing 10% FBS and 10% dimethyl sulfoxide (DMSO), frozen and stored, were used as the reacted cells after thawing and rinsing. The cultivation was carried out under the conditions of about 37° C. and 5% $CO_2$ for 7 days.

An even better cell proliferation was observed in this mixed culture solution when 50 U/mL of IL-2 was added. When the rate of cell proliferation was high, 100 U/mL of IL-2 and 1 mL of AIM-V medium containing 10% FBS were added on the $4^{th}$-$6^{th}$ day.

Seven days later the number of cells was measured using a hemocytometer, and the proportion of γδ T-cells using a flow cytometer. For the antibodies, PC5-labeled anti-CD3 and FITC-labeled anti-pan γ/δ antibodies (Beckman Coulter) were used. These antibodies were added to the cells that were cultured and washed with PBS for dying at 4° C. for 15 minutes in a shaded condition. The isotype of anti-pan γ/δ antibody was utilized as a negative control.

As shown in FIG. 1, it was found that, compared to the controls (dendritic cells not pulsed with bisphosphonate), all of the mature dendritic cells and immature dendritic cells pulsed with Aredia, Onclast, and Zometa increased the proportion of γδ T-cells in the cocultivated cell subsets.

Moreover, it was found that the immature cells pulsed with bisphosphonates increased the proportion of γδ T-cells more than the mature dendritic cells pulsed with bisphosphonates did.

Example 4

<Collection and Preparation of γδ T-Cells>

From a healthy donor 30 ml of peripheral blood was collected, and peripheral blood mononuclear cells were collected using a density gradient medium for blood cell separation. The cells collected were washed several times to remove platelets and the like.

The peripheral blood monocytes obtained were suspended in AIM-V medium (10% FCS), and Aredia was added so that the concentration in the peripheral blood monocyte suspension was 10 μM.

This was cultivated for 14 days. During this period, AIM-V (10% FCS) medium and IL-2, at a final concentration of 1,000 U/ml, were added in accordance with the cell proliferation.

Using a flow cytometer, the phenotype of the cells cultured was confirmed to be a cell subset containing at least 95% of γδ T-cells.

Example 5

<Confirmation of the Activation of γδ T-Cells>

In each well of a MultiScreen plate (Millipore), 70% ethanol was added and removed within two minutes.

Each well of the plate was washed with 200 μl of PBS five times.

An anti-interferon(IFN)-γ antibody for coating (clone: 1-D1K, MABTECH ELISpot for Human Interferon-γ kit) was diluted with PBS to 15 μg/ml, and added 100 μl/well.

The plate was left standing at 4° C. overnight.

The plate was washed with 200 μl/well of PBS four times.

AIM-V medium containing 10% FBS was added 200μl/well, and blocking was performed at room temperature for at least 30 minutes.

The blocking medium was removed and the plate was washed with 200 μl/well of PBS four times.

The γδ T-cells obtained in Example 4 were collected by centrifugation and washed twice with AIM-V.

To 30,000 of the γδ T-cells collected, and 15,000 of the immature or mature dendritic cells obtained in Example 1 Aredia, prepared to have a final concentration of 10 μM, was added, and precultivated in a 15 ml tube (Falcon) under the conditions of 37° C. and 5% $CO_2$ for two hours. At the same time, precultivation of γδ T-cells by themselves, precultivation of γδ T-cells with only Aredia added thereto, and precultivation of the respective dendritic cells by themselves were also conducted. Each culture volume was adjusted to 300 μl.

The plate was washed with PBS after blocking, and each group of cells which completed precultivation under the respective conditions was disseminated in three wells, 100 μl/well.

They were cultured overnight under the conditions of 37° C. and 5% $CO_2$.

The culture solution containing the cells was removed and the plate was washed five times with 200 μl/well of PBS.

Biotin-labeled anti-IFN-γ antibody for detection (clone: 7-B6-1, MABTECH ELISpot for Human Interferon-γ kit) was diluted to 1 μg/ml with PBS containing 0.5% FBS and added 100 μl/well.

The plate was left standing for two hours at room temperature.

The PBS containing Biotin-labeled anti-IFN-γ antibody was removed, and the plate was washed five times with 200 μl/well of PBS.

Alkaliphosphatase-bonded streptoabizine (MABTECH ELISpot for Human Interferon-γ kit) was diluted with PBS containing 0.5% FBS to 1:1000, and added 100 μl/well.

The plate was left standing for one hour at room temperature.

The plate was washed five times with 200 μl/well of PBS.

BCIP/NBTplus substrate stock solution (Wako) was added 100 μl/well; the plate was left standing in the dark until spots were recognizable.

When spots were visually recognized, the plate was washed thoroughly with distilled water.

After confirming that the membrane on the plate was dry, the number of spots was measured using an ELISpot reader (AID Autoimmune Diagnostika GmbH), and the data was analyzed using the AID software version 3.1 (AID).

The results showed that the number of spots and the spot intensity increased only when the dendritic cells and Aredia were added simultaneously to the γδ T-cells. The results also showed that the immature dendritic cells pulsed with the bisphosphonate stimulated the generation of IFN-γ more than the mature dendritic cells did.

POTENTIAL FOR INDUSTRIAL APPLICATION

As described above, the dendritic cells pulsed with bisphosphonates in the present invention are capable of selectively activating and/or proliferating the γδ T-cells contained in peripheral blood. Accordingly, they can be used as a composition capable of activating and/or proliferating γδ T-cells in vitro. Moreover, by administering them to a patient as an administrable composition, γδ T-cells can be activated in vivo, from which effective treatment of cancers and viral infections can be expected.

We claim:

1. Cultured, isolated dendritic cells having been in vitro pulsed with a bisphosphonate-based bone metabolism improving drug, wherein the cultured, isolated dendritic cells have enhanced functional activity for activating and/or proliferating γδ T-cells in culture in relation to cultured, isolated dendritic cells which have not been exposed to a bisphosphonate-based bone metabolism improving drug.

2. The cultured, isolated dendritic cells of claim 1, wherein said dendritic cells are immature dendritic cells.

3. The cultured, isolated dendritic cells of claim 1, wherein said bisphosphonate-based bone metabolism improving drug is selected from the group consisting of pamidronic acid, alendronic acid, zoledronic acid, risedronic acid, ibandronic acid, incadronic acid, etidronic acid, their salts and their hydrates.

4. A pharmaceutical composition comprising cultured, isolated dendritic cells in vitro pulsed with a bisphosphonate-based bone metabolism improving drug, wherein the cultured, isolated dendritic cells have enhanced functional activity for activating and/or proliferating γδ T-cells in culture in relation to cultured, isolated dendritic cells which have not been exposed to a bisphosphonate-based bone metabolism improving drug.

5. The pharmaceutical composition of claim 4, wherein said cultured, isolated dendritic cells are immature dendritic cells.

6. The pharmaceutical composition of claim 4, wherein said bisphosphonate-based bone metabolism improving drug is selected from the group consisting of pamidronic acid, alendronic acid, zoledronic acid, risedronic acid, ibandronic acid, incadronic acid, etidronic acid, their salts and their hydrates.

7. The cultured, isolated dendritic cells of claim 1, wherein said dendritic cells are a mixture of immature and mature dendritic cells.

8. The cultured, isolated dendritic cells of claim 1, wherein said dendritic cells have been in vitro pulsed with pamidronic acid or a salt or hydrate thereof.

9. The cultured, isolated dendritic cells of claim 1, wherein said dendritic cells have been in vitro pulsed with alendronic acid or a salt or hydrate thereof.

10. The cultured, isolated dendritic cells of claim 1, wherein said dendritic cells have been in vitro pulsed with zoledronic acid or a salt or hydrate thereof.

11. The pharmaceutical composition of claim 4, wherein said cultured, isolated dendritic cells have been in vitro pulsed with pamidronic acid or a salt or hydrate thereof.

12. The pharmaceutical composition of claim 4, wherein said cultured, isolated dendritic cells have been in vitro pulsed with alendronic acid or a salt or hydrate thereof.

13. The pharmaceutical composition of claim 4, wherein said cultured, isolated dendritic cells have been in vitro pulsed with zoledronic acid or a salt or hydrate thereof.

14. The cultured, isolated dendritic cells of claim 1, wherein the cultured, isolated dendritic cells are produced by a process comprising:
 a) differentiating precursor cells in vitro, wherein the precursor cells are selected from the group consisting of (i) isolated CD14 positive cells; (ii) isolated peripheral blood mononuclear cells; (iii) isolated CD34 positive hematopoietic stem cells; and (iv) a mixture thereof, to provide isolated, cultured dendritic cells; and
 b) pulsing the cultured isolated dendritic cells with a bisphosphonate-based bone metabolism improving drug.

15. The pharmaceutical composition of claim 4, wherein the cultured, isolated dendritic cells have been washed with a pharmaceutically-acceptable, isosmotic washing solution.

16. The pharmaceutical composition of claim 4, wherein the bisphosphonate-based bone metabolism improving drug is pamidronate disodium pentahydrate.

17. The pharmaceutical composition of claim 4, wherein the bisphosphonate-based bone metabolism improving drug is alendronate sodium trihydrate.

18. The pharmaceutical composition of claim 4, wherein the bisphosphonate-based bone metabolism improving drug is zoledronate sodium hydrate.

* * * * *

UNITED STATES PATENT AND TRADEMARK OFFICE
CERTIFICATE OF CORRECTION

PATENT NO.       : 8,513,010 B2                                              Page 1 of 1
APPLICATION NO. : 11/631660
DATED            : August 20, 2013
INVENTOR(S)      : Nieda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1197 days.

Signed and Sealed this
Fifteenth Day of September, 2015

Michelle K. Lee
*Director of the United States Patent and Trademark Office*